(12) United States Patent
Lee et al.

(10) Patent No.: US 6,465,680 B2
(45) Date of Patent: Oct. 15, 2002

(54) PROCESS FOR PREPARING MALONATE DERIVATIVES OR β-KETO ESTERS FROM EPOXIDE DERIVATIVES

(75) Inventors: Byeong No Lee, Seoul; In-Sun Jung; Eun Joo Jang, both of Daejun-Shi, all of (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 09/884,440

(22) Filed: Jun. 20, 2001

(65) Prior Publication Data

US 2002/0035290 A1 Mar. 21, 2002

(30) Foreign Application Priority Data

Jun. 20, 2000 (KR) .............................. 00-33905

(51) Int. Cl.$^7$ .............................. C07C 69/66
(52) U.S. Cl. .................. 560/179; 560/180; 560/175; 562/517; 562/538; 562/579; 562/590
(58) Field of Search .................. 560/179, 178, 560/180, 174, 190, 175; 562/523, 524, 525, 538, 517, 579, 590

(56) References Cited

U.S. PATENT DOCUMENTS

| | | | | |
|---|---|---|---|---|
| 3,892,787 A | | 7/1975 | Gutierrez et al. ........ 260/410.9 |
| 4,443,624 A | | 4/1984 | Prange et al. ................ 560/204 |
| 4,620,033 A | * | 10/1986 | Isshiki et al. ................ 562/519 |
| 5,723,389 A | | 3/1998 | Slaugh et al. ................ 568/862 |
| 5,731,478 A | | 3/1998 | Slaugh et al. ................ 568/862 |
| 5,770,776 A | | 6/1998 | Powell et al. ................ 568/862 |
| 5,817,870 A | * | 10/1998 | Haas et al. .................. 562/531 |
| 5,886,219 A | * | 3/1999 | Steffen ........................ 562/590 |

FOREIGN PATENT DOCUMENTS

| | | | | |
|---|---|---|---|---|
| DE | 25 24 389 | | 12/1976 | ........... C07C/69/38 |
| JP | 56-5433 | | 1/1981 | ........... C07C/55/08 |
| JP | 08092156 | * | 4/1996 | ......... C07C/59/245 |
| KR | 2000-5357 | | 2/2000 | |
| WO | WO 99/08988 | * | 2/1999 | ........... C07C/51/08 |

OTHER PUBLICATIONS

Klaus Hinterding et al, "Regioselective Carbomethoxylation of Chiral Epoxides: A New Route to Enantiomerically Pure β–Hydroxy Esters", J. Org. Chem., vol. 64 (1999), pp. 2164–2165.*

* cited by examiner

*Primary Examiner*—Paul J. Killos
(74) *Attorney, Agent, or Firm*—Lee & Sterba, P.C.

(57) ABSTRACT

A process for preparing a malonic acid monoester or β-ketoester from an epoxide includes the steps of reacting an epoxide with carbon monoxide and an alcohol in the presence of a catalytic amount of a cobalt compound and at least one promoter to produce a β-hydroxyester, separating the β-hydroxyester from the cobalt compound and the promoter, and oxidizing the β-hydroxyester to produce a malonic acid monoester or β-ketoester.

26 Claims, 1 Drawing Sheet

Synthesis of malonate derivatives and β-ketoester derivatives from carbonylation of epoxides

PROCESS FOR PREPARING MALONATE DERIVATIVES OR β-KETO ESTERS FROM EPOXIDE DERIVATIVES

FIELD OF THE INVENTION

The present invention relates to a process for preparing malonate derivatives or β-ketoesters by carbonylating an epoxide derivative to prepare a β-hydroxyester and then oxidizing the resulting β-hydroxyester. More specifically, the present invention relates to a process for preparing malonate derivatives or β-ketoesters by reacting an epoxide derivative with carbon monoxide and an alcohol in the presence of a catalyst system comprising a cobalt catalyst and a promoter to produce a β-hydroxyester and then oxidizing the resulting β-hydroxyester.

BACKGROUND OF THE INVENTION

Epoxide derivatives can be readily converted into a difunctional compound via carbonylation so that they can be used as an intermediate compound for preparing useful organic compounds. Particularly, since a 3-hydroxyester derivative has two functional groups, it has been known that it can be used as a solvent, a resin and a coating material. Further, it can be used as a raw material for pharmaceutical compounds due to its easy convertibility into other compounds, and it can also be used as an intermediate for the synthesis of alkanediols, which are the raw material for polyesters. In this regard, alkanediols are widely used as intermediates in coatings or in organic synthesis, as well as the raw materials for the synthesis of polyesters. Such 1,3-diols have generally been prepared through the hydrogenation of 3-hydroxyaldehyde derivatives which are prepared by hydroformylation of epoxide derivatives (see, e.g. U.S. Pat. Nos. 5,770,776, 5,723,389 and 5,731,478).

The present have already developed a novel process for obtaining 1,3-alkanediols in a high yield, in which an epoxide derivative is hydroesterified to synthesize a 3-hydroxyester derivative and the resulting ester intermediate is reacted with hydrogen, as well as a catalyst system useful for hydroesterification in this process, both of which are the subject of Korean Patent Application No. 2000-5357 dated Feb. 3, 2000. The present inventors have also found that malonate derivatives and β-ketoesters can be synthesized in a high yield at a low cost by oxidizing or hydrolyzing β-hydroxyesters under suitable conditions, and thus achieved the present invention.

Malonic acid and its derivatives, including malonate, cyanoacetate, cyanoacetic acid, malonitrile, etc., are very important compounds in the industrial field. Since such $C_3$-dicarboxylic acid-type compounds can be used as raw materials for synthesizing derivatives such as pyrimidines, purines, etc., and further, as the starting material for numerous groups of compounds such as pharmaceuticals, flavoring agents, dyes, etc., due to their high reactivity, they have a high marketability.

Prior methods for synthesis of malonates can be summarized by the following reaction schemes. Typical examples include the hydrogen cyanide process using hydrogen cyanide and chloroacetic acid and the carbon monoxide process incorporating carbon monoxide into chloroacetate ester, as disclosed in German Patent No. 2,524,389. However, the hydrogen cyanide process has disadvantages in that it produces many other side products and also much waste water, and furthermore, noxious gases generated during the procedure are difficult to treat. Its economic practicability is lowered in all aspects, although it has some advantages in that the procedure is relatively simple and the overall yield reaches about 75–85%. Meanwhile, in the carbon monoxide process the reaction can be practiced in a good yield under mild conditions (20–80° C., 0.12~1.0 Mpa) with a conversion rate of about 90% and a selectivity of about 95%. However, the carbon monoxide process has disadvantages in that the raw materials used in this procedure are expensive, and it also produces side products including chlorides, etc., and thus is economically undesirable (see Ullmann Encyclopedia, Vol. A16, p63).

1. The hydrogen cyanide process

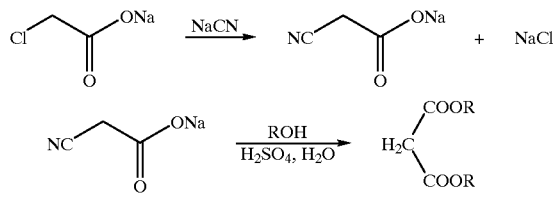

2. The carbon monoxide process (SFC)

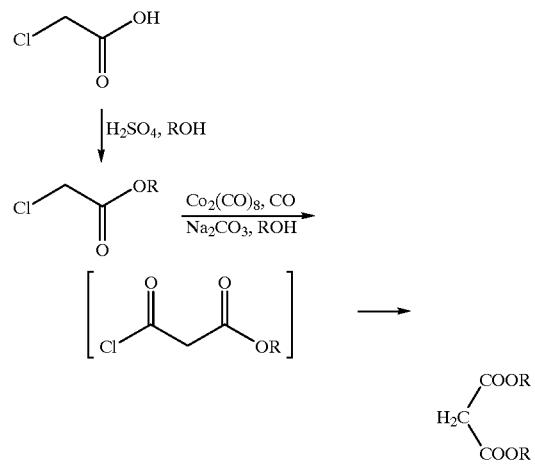

In the above reaction schemes, R represents $CH_3$, $C_2H_5$ or $C_3H_7$.

In addition to the above processes, other known processes include the method of reacting ketene with carbon monoxide, the method of synthesizing malonic acid from potassium acetate and carbon monoxide in the presence of calcium carbonate and successively esterifying malonic acid, and the method of synthesizing malonic acid monoester by reacting acetate ester with carbon monoxide in the presence of alkali metal phenoxide, etc.. The method using ketene synthesizes the desired product from the very expensive and toxic starting material; and in the method starting from acetate ester, dimethylformamide used in the reaction is very toxic and difficult to remove from the resulting product, and diazomethane, which is also used together therewith, has been assumed to be a carcinogenic material and is also explosive; furthermore, the raw materials used in this method are very expensive. Alternatively, the method using carboxylation from 1,3-propanediol (see, U.S. Pat. No. 3,892,787) and the method for synthesis of malonic acid from 1,3-propanediol via oxidation (Japanese Laid-open Patent Publication No. Sho 56-5433) have also been disclosed. However, these methods are disadvantageous in that the starting material is very expensive. In addition, the method utilizing oxidation of propene with an electrochemical catalyst has been disclosed but has not been widely used industrially.

As can be clearly seen from the above, the process for preparing malonic acid derivatives or β-ketoester derivatives, which comprises the steps of hydroesterifying an ethylene oxide derivative to synthesize a β-hydroxyester intermediate, oxidizing the resulting ester intermediate and then adding an acid or a base or the corresponding acidic or alkaline resins thereto, has never been disclosed heretofore in the relevant technical field.

SUMMARY OF THE INVENTION

A feature of the present invention is to provide a novel process for preparing malonate derivatives or β-ketoesters in a high yield, by reacting an epoxide derivative with carbon monoxide and an alcohol in the presence of a catalyst system consisting of a cobalt catalyst and a promoter to effectively produce a β-hydroxyester, and then oxidizing the resulting β-hydroxyester.

Another feature of the present invention is to provide a novel process for preparing malonate derivatives or β-ketoesters in a high yield by developing a catalyst system comprising a cobalt catalyst and a promoter, which has a high activity and selectivity in carbonylation for converting an epoxide derivative into a β-hydroxyester via reaction with carbon monoxide and an alcohol.

Still another feature of the present invention is to provide a novel process for preparing malonate derivatives or β-ketoesters, in which the cost of the catalyst can be reduced by using imidazole or a derivative thereof as a promoter.

In accordance with one aspect of the present invention, there is provided a process for preparing a malonic acid monoester or β-ketoester from an epoxide. The process includes the steps of (a) reacting an epoxide with carbon monoxide and an alcohol in the presence of a catalytic amount of a cobalt compound and at least one promoter to produce a β-hydroxyester; (b) separating the β-hydroxyester from the cobalt compound; and (c) oxidizing the β-hydroxyester to produce a malonic acid monoester or β-ketoester.

In specific embodiments, the promoter used in the step (a) is an imidazole derivative.

According to another particular embodiment, the epoxide is represented by the following formula (II):

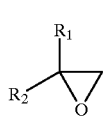

(II)

wherein $R_1$ and $R_2$ are independently a hydrogen atom; a $C_{1-20}$ linear or branched alkyl group, a $C_{5-10}$ cycloalkyl group, a $C_{6-20}$ alkylcycloalkyl group, a $C_{6-20}$ (cycloalkyl)alkyl group, a $C_{7-20}$ aralkyl group, or a $C_{7-20}$ alkaryl group, each of which can be unsubstituted or substituted with at least one F, Cl or Br; or a $C_{6-20}$ aryl group which is unsubstituted or substituted with at least one F, Cl, amine group, nitrile group or alkoxy group.

In a further particular embodiment, in step (c) the β-hydroxyester is oxidized in the presence of an oxidizing catalyst. According to still other particular embodiments, step (c) is carried out in the presence of a promoter. More specific embodiments recycle the oxidizing catalyst and the promoter after step (c).

According to one specific embodiment, $R_1$ and $R_2$ in the epoxide are hydrogen atoms, and in step (c) the β-hydroxyester is oxidized to yield a malonic acid monoester. In a more particular embodiment, the malonic acid monoester is then reacted in the presence of an acid or base with an alcohol to yield a malonic acid diester. In another more particular embodiment, the malonic acid monoester is then hydrolyzed in the presence of an acid to yield malonic acid. In a further more particular embodiment, the malonic acid monoester is then hydrolyzed in the presence of a base to yield a malonic acid dianion.

In another particular embodiment, the malonic acid monoester is reacted with an alkaline base to form a salt of the malonic acid monoester.

According to another specific embodiment, $R_1$ and $R_2$ in the epoxide are not hydrogen atoms and $R_2$ is not a hydroxymethyl group, and in step (c) the β-hydroxyester is oxidized to yield a β-ketoester.

Other feature and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWING

The present invention will be more clearly understood by reference to the description which follows when taken together with the attached drawing in which.

DETAILED DESCRIPTION OF THE INVENTION

Figure 1:
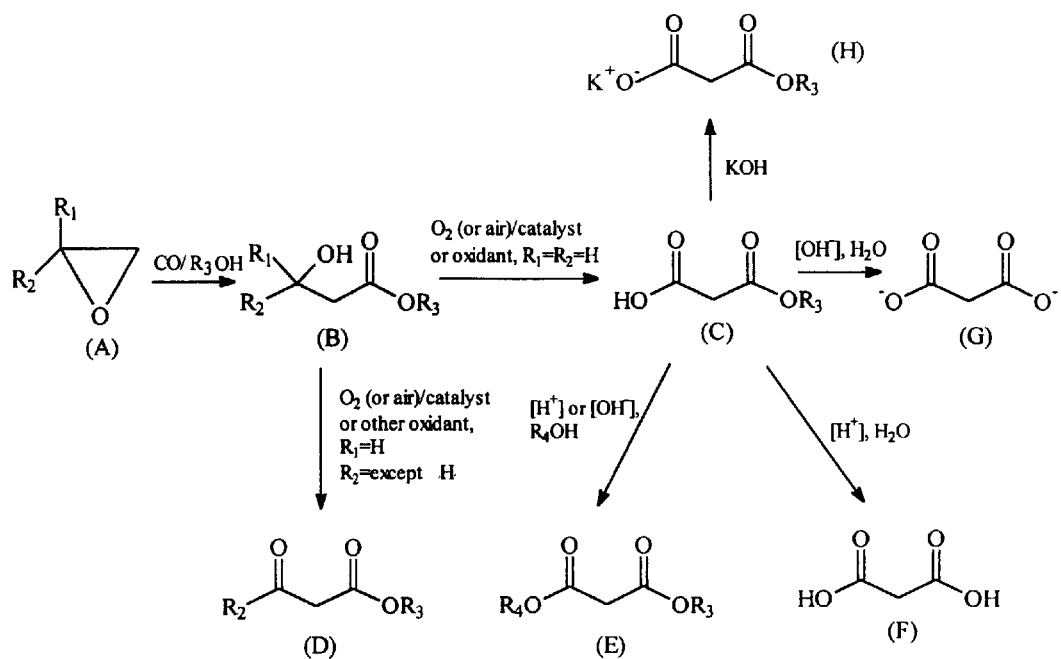
FIG. 1 shows an outline reaction scheme describing a process for preparing malonate derivatives or β-ketoesters from epoxide derivatives according to the present invention.

The priority Korean Patent Application No. 2000-33905, filed Jun. 20, 2000, is hereby incorporated in its entirety by reference.

The present invention relates to a process for preparing malonate derivatives or β-ketoester derivatives which comprises the steps of hydroesterifying an epoxide derivative to synthesize a β-hydroxyester intermediate and then oxidizing the resulting ester intermediate (see FIG. 1).

The present invention achieves an increased yield of β-hydroxyester by means of an effective catalyst system. For this purpose, in the hydroesterification of the epoxide derivative, a catalyst system, more specifically a cobalt catalyst such as $Co_2(CO)_8$ used alone or in a mixture with a promoter, for example, imidazole, pyridine, pyrrole, pyrazine, pyrazole, pyrimidine, piperidine or a derivative thereof, can be used, provided that the promoter compound combined with a phosphine-based compound is not used in this catalyst system.

In preferred embodiments of the catalyst system according to the invention, the molar ratio of the promoter to the cobalt compound is in the range from 0.01:1 to about 100:1.

In preferred embodiments of the present invention, an imidazole derivative represented by the following formula (I) is used as the promoter:

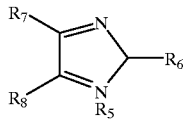
(I)

wherein $R_5$, $R_6$, $R_7$ and $R_8$ are independently a hydrogen atom; a $C_{1-10}$ linear or branched alkyl, $C_{5-10}$ cycloalkyl, $C_{6-10}$ alkylcycloalkyl, $C_{6-10}$ (cycloalkyl)alkyl, $C_{7-10}$ alkaryl or $C_{7-10}$ aralkyl group which is unsubstituted or substituted with a hydroxy group; F; Cl; a $C_{1-3}$ alkoxy group; or a hydroxy group.

Imidazole and its derivatives are inexpensive so that the cost of the catalyst can be reduced.

The reaction preferably is carried out in a suitable solvent in the presence of an alcohol at a temperature ranging from about 30 to about 150° C., preferably about 40 to about 120° C., under CO pressure of about 50 to about 3000 psig, preferably about 100 to about 1500 psig.

The epoxide derivative is represented by the following formula (II):

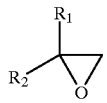
(II)

wherein $R_1$ and $R_2$ are independently a hydrogen atom; a $C_{1-20}$ linear or branched alkyl group, a $C_{5-10}$ cycloalkyl group, a $C_{6-20}$ alkylcycloalkyl group, a $C_{6-20}$ (cycloalkyl)alkyl group, a $C_{7-20}$ aralkyl group, or a $C_{7-20}$ alkaryl group, each of which can be unsubstituted or substituted with at least one F, Cl or Br; or a $C_{6-20}$ aryl group which is unsubstituted or substituted with at least one of F, Cl, amine, nitrile or alkoxy group.

Preferred examples of the epoxide derivatives include ethylene oxide, propylene oxide, 1-butene oxide, 1-pentene oxide, 1-heptene oxide, 1-octene oxide, 1-nonene oxide, 1-decene oxide, 2-methyl-propylene oxide, epifluorohydrin, epichlorohydrin, epibromohydrin, glycidol, methyl glycidate, ethyl glycidate, t-butyl glycidate, 2-methyl-1-butene oxide, 2-methyl-1-pentene oxide, 2-methyl-1-hexene oxide, 2-methyl-1-heptene oxide, 2-methyl-1-octene oxide, 2-methyl-1-nonene oxide, 2-methyl-1-decene oxide, 2-ethyl-1-butene oxide, 2-ethyl-1-pentene oxide, 2-ethyl--hexene oxide, 2-ethyl-1-heptene oxide, 2-ethyl-1-octene oxide, 2-ethyl-1-nonene oxide, 2-ethyl-1-decene oxide, allyl benzene oxide, styrene oxide, etc.

The alcohol is represented by the formula $R_3OH$, in which $R_3$ is $C_{1-20}$ linear or branched alkyl group, a $C_{5-20}$ cycloalkyl group, a $C_{6-20}$ aryl group, a $C_{7-20}$ alkaryl group or a $C_{7-20}$ aralkyl group. It is preferably methyl, ethyl, isopropyl, cyclohexyl, phenyl or benzyl alcohol.

As a solvent for the above reaction, ether compounds, substituted aromatic compounds or acetate compounds can be additionally used, or alternatively, the $R_3OH$ compound itself can be used as the solvent.

The ether compounds preferably have a structure represented by the following formulas (III), (IV) or (V):

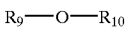
(III)

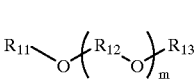
(IV)

(V)

wherein $R_9$, $R_{10}$, $R_{11}$, $R_{12}$ and $R_{13}$ are independently a $C_{1-10}$ unbranched or branched alkyl group, a $C_{5-10}$ cycloalkyl group, a $C_{6-10}$ alkylcycloalkyl group, a $C_{6-10}$ (cycloalkyl)alkyl group, a $C_{7-10}$ aralkyl group, or a $C_{7-10}$ alkaryl group; m is an integer from 1 to 10; and n is an integer from 2 to 5.

The β-hydroxyester compounds (B) synthesized from epoxide derivatives are represented by the following formula (VI):

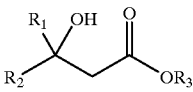
(VI)

The resulting products (C) and (D) from oxidation of the compound (B) of formula (VI) are represented by the following formulas VII and VIII, respectively:

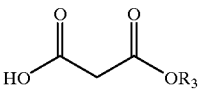
(VII)

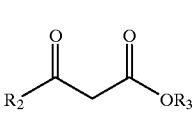
(VIII)

The oxidation of β-hydroxyester compounds to prepare the products (C) and (D) can be carried out at the temperature ranging from about 10 to about 350° C., preferably from about 20 to about 110° C. The reaction can be carried out under an oxygen pressure of about 5 to about 3000 psig, preferably from about 150 to about 1500 psig. In addition, the oxidization using an oxidizing catalyst such as platinum can be carried out in a suitable organic solvent, as well as water. The organic solvents that can be used in this reaction includes, without limitation, $C_{1-20}$ unbranched or branched alkanes, $C_{5-20}$ cycloalkanes, $C_{6-20}$ aromatic compounds, $C_{6-20}$ alkylcycloalkanes, $C_{6-20}$ (cycloalkyl)alkanes, $C_{7-20}$ alkyl-substituted aromatic compounds, and $C_{7-20}$ aryl-substituted alkanes, each of which can also further substituted with F, Cl, ester groups or alkoxy groups; ethers represented by the formulas R'OR" or R'—O—(R"O)—R''', wherein R', R" and R''' represent $C_{1-20}$ alkyl groups; cyclic ethers; and esters. Preferred examples of the solvent which can be used in this reaction includes tetrahydrofuran, dioxane and ethyl acetate.

Furthermore, an acid or base stable under the conditions of the oxidation reaction can be added to increase the reaction rate.

The oxidizing catalyst which can be used for this purpose generally includes noble metals such as platinum (including those obtained from reduction of platinum oxide with hydrogen), rhodium, palladium, Raney nickel, etc., transition metals such as vanadium, etc., noble metals or transition metals adsorbed on solid supports, mixed catalysts containing said metals and said mixed catalysts adsorbed on solid supports. In other words, it is understood that the catalyst commonly refers to all of the catalysts comprising noble metals or transition metal compounds such as $H_2PtCl_6$, $Pt(NH_3)_4(OH)_2$, $Rh(NO_3)_3$, palladium (II) chloride, etc., or catalysts formed by adsorbing said metals on solid supports. In addition, as well as said heterogeneous catalysts, general oxidants, for example, hydrogen peroxide, lead tetraacetate $(Pb(OCOCH_3)_4)$, chromium trioxide, complexes of chromium trioxide with pyridine or pyrazole, pyridinium chlorochromate, potassium dichromate, pyridium dichromate, potassium permanganate, etc., can also be used. In the catalyst system, the ratio of the oxidizing catalyst to the separated product is in a range of about 1:10 to about 1:1000.

Furthermore, a promoter such as Bi, Pb, oxides, carbonates or phosphates forms of said metals, a mixture of 1,10-phenanthroline and dialkyl diazodicarboxylate, etc., can be added into the oxidization reaction. The ratio of the oxidizing catalyst to the promoter, if used, ranges up to about 1:10.

Even though the oxidation conditions are the same in the above reaction, malonic acid monoester (C) is produced when $R_1$ and $R_2$ are hydrogen atoms and β-hydroxyester is in the type of primary alcohol, and the β-ketoester (D) is produced when one of $R_1$ and $R_2$ is hydrogen and the other is a substituent other than hydrogen.

The oxidized product (C) can be reacted with the acid or base in an alcohol solvent or distilled water to produce the compounds (E), (F) and (G), which are represented by the following formulas (IX), (X) and (XI), respectively:

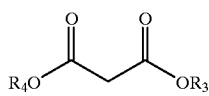

(IX)

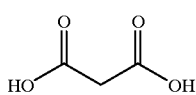

(X)

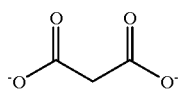

(XI)

The alcohols used in synthesizing the compound (E), represented by formula (IX), are represented by the formula $R_4OH$, wherein $R_4$ is a $C_{1-10}$ unbranched or branched alkyl group, a $C_{5-10}$ cycloalkyl group, a $C_{6-10}$ alkylcycloalkyl group, a $C_{6-10}$ (cycloalkyl)alkyl group, or a $C_{7-10}$ aralkyl group.

In addition, the acids used for preparing the compounds (E)–(F) include all strong and weak acids, for example, sulfuric acid, hydrochloric acid, nitric acid, acetic acid, HF, $H_3PO_4$, perchloric acid, p-toluenesulfonic acid, trifluoromethylsulfonic acid, etc., and further, the corresponding acidic polymers, for example, weak acidic materials such as Amberlite IR-120, Dowex 50, Permutit RS, Permutit C 50D, Zeolit 225, CM-Sephadex C-25 or C-50, or strong acidic materials such as Amberlite IRC-50, Permutit C, Permutit H or H-70, Zeolit 236, SP-Sephadex C-25 or C-50. Similarly, the bases which can be used for such a purpose include weak bases such as pyridine, alkaline bases such as sodium hydroxide, potassium hydroxide, sodium bicarbonate, sodium carbonate, potassium carbonate, calcium hydroxide, etc., basic resins, for example, weak base materials such as Amberlite IR-4B or 45, Dowex 3, Permutit E, Permutit A 240A, DEAE-Sephadex A-25 or A-50, etc., or strong base materials such as Amberlite IRA-400, Dowex 1, Permutit ESB, Permutit A 330D, Zeolit FF, QAE-Sephadex A-25 or A-50, etc. In the present invention, such acids or bases can be used together with solid supports such as charcoal, silica, etc.

To synthesize the compound (E) from compound (C), esterification preferably is carried out with the acid or base in an alcohol solvent at the temperature ranging from about 20 to about 110° C. The reaction can preferably be practiced under a nitrogen or argon atmosphere although it may be practiced in air. In addition, the acid or base can be used in an excessive amount relative to the catalytic amount, which is encompassed within the scope of the present invention. In a similar manner, the compound (F), i.e. malonic acid, is synthesized via hydrolysis using the acid in distilled water and the compound (G), i.e. malonic acid salt, is synthesized via hydrolysis using the base. In the process of synthesizing malonic acid or malonic acid salts, the temperature should not be excessively increased because heating above 70° C. may cause decarboxylation. It will be understood that the esterification and hydrolysis as mentioned above can be practiced using excessive to very small amounts of acid or base and further, the corresponding polymers, all of which are included in the present invention.

Since the derivatives synthesized according to the present invention have two functional groups, they themselves can be utilized as intermediates for organic synthesis or as coating materials, and further, can readily be converted into various derivatives.

The present invention is very valuable in that 1,3-diol compounds can be obtained in a cheap and economical manner from hydrogenation of the β-hydroxyester intermediate, and when one of $R_1$ and $R_2$ in the product (C) and (D) prepared by oxidation of β-hydroxyester intermediates is particularly $CH_2Cl$, that is, an epichlorohydrin type compound is used as the starting material, compounds containing three kinds of functional groups at four carbon atoms can be obtained. In this case, the resulting β-hydroxyester is subjected to dehydrogenation to obtain 4-chloroacetylacetonate, which currently has been synthesized from di-ketene in the industrial field. Therefore, the present invention has an important advantage in that it can provide numerous compounds very useful in the industrial field under similar reaction conditions.

The compound (C) of formula (VII) can also be reacted with KOH to obtain the compound (H) represented by the following formula (XIII):

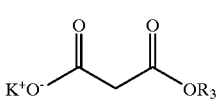

(XIII)

The present invention can be more clearly understood by referring to the following examples. It should be understood that the following examples are not intended to restrict the scope of the present invention in any manner.

EXAMPLES 1–10

Hydroesterification of ethylene oxide with $Co_2(CO)_8$ catalyst in the presence of imidazole The specific contents of these examples are summarized in the following Table 1. In a 450 ml Parr reactor, a predetermined amount of the solvent was introduced at room temperature under a nitrogen atmosphere and then $Co_2(CO)_8$ was added thereto. CO gas was supplied to the reactor to a pressure of 500 psig, and then the reaction mixture was heated to 80° C. and stirred for one hour. Then, the reaction solution was cooled and degassed, and a predetermined amount of imidazole as the promoter was added thereto. Ethylene oxide was added to the reactor, and then a predetermined pressure was applied to the reactor. The temperature was elevated to that as given in Table 1, and then the reaction was carried out for a predetermined period. During the reaction, a reaction sample was taken by means of a tube and the resulting product, methyl 3-hydroxypropionate (3-HPM), was analyzed with GC. When the reaction was completed, the temperature was lowered to room temperature, and the resulting product was separated, with removal of the catalyst, and then quantitatively analyzed.

EXAMPLES 16A–16E

Oxidation of methyl 3-hydroxypropionate

These examples relate to the oxidation of methyl 3-hydroxypropionate in the presence of water and oxygen by means of a platinum catalyst not containing any promoter, and examine the effect of temperature and also the effects of changes in time and oxygen pressure. The amounts of catalyst as given in the following Table 3 are described in the mmol unit of metal atom for quantitative comparison.

In a 45 ml Parr autoclave purged with nitrogen, platinum oxide hydrate (~80–81% Pt) was introduced and then 10 ml

TABLE 1

Hydroesterification of ethylene oxide with $Co_2(CO)_8$ catalyst in the presence of imidazole

| Ex. | Catalyst | Temp (° C.) | Pressure (bar) | Reaction time (hr) | MeOH (ml) | Conversion rate (%) | Yield[4] (%) 3-HMP | Selectivity[5] (mol %) 3-HMP | AA | DMA | ME | Dimer |
|---|---|---|---|---|---|---|---|---|---|---|---|---|
| 1 | $Co_2(CO)_8$ | 70 | 34 | 3 | 200 | 78.09 | 65.72 | 84.16 | 2.12 | 7.38 | 0.86 | 2.08 |
| 2 | $Co_2(CO)_8$ | 70 | 50 | 3 | 200 | 68.23 | 60.53 | 88.70 | 5.38 | 0.14 | 1.65 | 1.5 |
| 3 | $Co_2(CO)_8$ | 70 | 80 | 3 | 200 | 65.66 | 57.43 | 87.50 | 2.89 | 0.38 | 1.59 | 2 |
| 4 | $Co_2(CO)_8$ | 60 | 50 | 3 | 200 | 45.19 | 38.52 | 85.24 | 3.66 | 0.17 | 0.95 | 0 |
| 5 | $Co_2(CO)_8$ | 75 | 50 | 3 | 200 | 78.62 | 66.0 | 84.0 | 0.02 | 8.63 | 1.51 | 2.44 |
| 6 | $Co_2(CO)_8$ | 80 | 50 | 3 | 200 | 91.61 | 68.68 | 75.0 | 8.27 | 5.70 | 2.30 | 2.60 |
| 7 | $Co_2(CO)_8$ | 80 | 34 | 2 | 100[1] | — | 82.44[6] | — | — | — | 0.65 | 3.75 |
| 8[2] | $Co_2(CO)_8$ | 80 | 34 | 4 | 250 | — | 70.1[6] | — | — | — | 4.75 | 1.78 |
| 9[3] | $Co_2(CO)_8$ | 80 | 34 | 4 | 200 | — | 66.4[6] | — | — | — | — | — |
| 10 | $Co_2(CO)_8$ | 75 | 60 | 3 | 150 | 95.27 | 88.90 | 93.31 | 1.78 | 0.32 | 0.98 | 3.61 |

Note)
Catalyst = 5 mmol; Imidazole = 20 mmol; Ethylene oxide = 500 mmol
[1]Methanol 100 ml + Tetraglyme
[2]Imidazole 40 mmol
[3]Ethylene oxide 1.4 mmol
[4]Yield = Selectivity × Conversion rate
[5]3-HPM = methyl 3-hydroxypropionate or 3-hydroxypropionic acid methyl ester
AA = acetaldehyde
DMA = acetaldehyde dimethyl acetal
ME = methoxyethanol
Dimer = $HOCH_2CH_2C(O)OCH_2CH_2(O)OCH_3$
[6]Isolated yield

EXAMPLES 11–15

Hydroesterification of other epoxide derivatives

The procedures of Examples 11 to 15 were conducted in the same manner as in the above Example 1, except that other oxide derivatives were used instead of ethylene oxide. The results are described in the following Table 2.

of distilled water was added thereto. The hydrogen pressure of the reactor was raised to 200 psig, the reactor was stirred for 2 hours, and hydrogen gas was then removed. Methyl 3-hydroxypropionate (1.0 g, 9.9 mmol) was added to the reactor, and the evacuation and filling with nitrogen were repeated three times. Then, the Parr autoclave was filled with

TABLE 2

| Ex. | Catalyst | Promoter | Epoxide | Product | Yield[1] (%) |
|---|---|---|---|---|---|
| 11 | $Co_2(CO)_8$ | Imidazole | Propylene oxide | methyl 3-hydroxybutanoate | 60.56 |
| 12 | $Co_2(CO)_8$ | Imidazole | Butylene oxide | methyl 3-hydroxypentanoate | 53.70 |
| 13 | $Co_2(CO)_8$ | Imidazole | Epichlorohydrin | methyl 3-hydroxy-4-chlorobutanoate | 66.17 |
| 14 | $Co_2(CO)_8$ | Imidazole | Glycidol | 3-hydroxy-γ-butyrolactone | 62.50 |
| 15 | $Co_2(CO)_8$ | Imidazole | Allylbenzene oxide | Methyl 3-hydroxy-4-phenylbutanoate | 91.20 |

Note)
Catalyst = 5 mmol; Promoter = 10 mmol; Epoxide = 500 mmol;
Temperature = 80° C.; Pressure = 34 bar; Reaction time = 4 hr;
Solvent = MeOH (200 ml)
[1]Isolated yield oxygen to a pressure of 55–90 bar. The reaction mixture was allowed to react for 18 hours while maintaining a temperature of 60–80° C. The reaction solution was filtered through celite or silica gel to remove heterogeneous catalyst, and the filtrate was directly distilled under reduced pressure. (Alternatively, it can be extracted with ethyl acetate and water and the separated organic layer and then dried over anhydrous magnesium sulfate and filtered, after which the organic layer is distilled under reduced pressure.) The resulting product was analyzed with gas chromatography, GC-MS and $^1$H-NMR.

EXAMPLE 20
Hydrolysis of malonic acid monomethyl ester

This example relates to a synthesis of the sodium salt of malonic acid (formula (XI)). Malonic acid monomethyl ester (0.5 g) obtained from Example 16 was reacted with aqueous sodium hydroxide solution (0.5 g of NaOH in 15 ml of water) for 12 hours to produce the sodium salt of malonic acid. $^1$H-NMR and gas chromatography analysis of the resulting product showed that the conversion rate and yield were 90% or more, respectively.

TABLE 3

| Ex. | HPM:PtO$_2$ | P$_{O2}$ (bar) | Temp. (° C.) | Time (h) | Yield (%) HPM$^{b)}$ | Acid$^{b)}$ | Aldehyde$^{b)}$ | Solvent | Condition$^{a)}$ |
|---|---|---|---|---|---|---|---|---|---|
| 16A | 10:1 | 90 | 60 | 24 h | 63% | 36% | 1% | Ethyl Acetate | H$_2$: 200 psig for 2 h |
| 16B | 10:1 | 90 | 60 | 24 h | — | 99% | — | Water | H$_2$: 200 psig for 2 h |
| 16C | 10:1 | 70 | 80 | 24 h | 1% | 99% | — | Water | H$_2$: 300 psig for 2 h |
| 16D | 20:1 | 70 | 80 | 18 h | 23% | 77% | trace | Water | H$_2$: 200 psig for 2 h |
| 16E | 100:1 | 70 | 60 | 18 h | 82% | 18% | trace | Water | H$_2$: 200 psig for 1 h |

Note)
$^{a)}$reduction condition with platinum oxide (PtO$_2$)
$^{b)}$HPM = methyl 3-hydroxypropionate or 3-hydroxypropionic acid methyl ester
Acid = malonic acid monomethyl ester
Aldehyde = H(CO)CH$_2$CH$_2$COOMe

EXAMPLE 17
Esterification of malonic acid monomethyl ester (basic condition)

This example relates to a synthesis of methyl malonate (formula (IX)) under a basic condition. Malonic acid monomethyl ester (0.5 g) obtained from Example 16 was added to pyridine and alcohol (pyridine 0.2 ml, methanol 15 ml) and allowed to react together for 12 hours at 50° C. under argon to produce methyl malonate. $^1$H—NMR and gas chromatography analysis of the resulting product showed that the conversion rate and yield were 95% or more, respectively.

EXAMPLE 18
Esterification of malonic acid monomethyl ester (acidic condition)

This example relates to a synthesis of methyl malonate (formula (IX)) under an acidic condition. Malonic acid monomethyl ester (0.5 g) obtained from Example 16 was added to acid and alcohol (conc. hydrogen chloride 0.1 ml, methanol 15 ml) and allowed to react together for 12 hours at 50° C. under argon to produce methyl malonate. $^1$H-NMR and gas chromatography analysis of the resulting product showed that the conversion rate and yield were 95% or more, respectively.

EXAMPLE 19
Hydrolysis of malonic acid monomethyl ester

This example relates to a synthesis of malonic acid (formula (X)). Malonic acid monomethyl ester (0.5 g) obtained from Example 16 was reacted with an acidic resin (Dowex 50WX2-200 ion exchange resin, 1.0 g) in 15 ml of distilled water for 12 hours to produce malonic acid. $^1$H-NMR and gas chromatography analysis of the resulting product showed that the conversion rate and yield were 90% or more, respectively.

EXAMPLE 21A–21D
The synthesis of methyl acetoacetate

EXAMPLE 21A
Oxidation of methyl 3-hydroxybutanoate in water

These examples relate to the oxidation of methyl 3-hydroxybutanoate in the presence of water and oxygen by means of a platinum catalyst not containing any promoter. In a 45 ml Parr autoclave purged with nitrogen, first platinum oxide hydrate (96 mg) was introduced, and then 3 ml of distilled water was added thereto. The hydrogen pressure in the reactor was increased to 500 psig, the reactor was stirred for 1 hour at room temperature, and hydrogen gas was then removed. Methyl 3-hydroxybutanoate (0.2 g, 1.69 mmol) was added to the reactor, and the evacuation and filling with nitrogen were repeated three times. Then, the Parr autoclave was filled with oxygen to a pressure of 60 bar. The reaction mixture was allowed to react for 100 hours or more at 25° C. The resulting product was analyzed by gas chromatography, GC-MS and $^1$H-NMR; conversion 95%, selectivity 99%.

EXAMPLE 21B–21D
Oxidation of methyl 3-hydroxybutanoate without water

In a 45 ml Parr autoclave purged with nitrogen, platinum oxide hydrate (~80–81% Pt) and methyl 3-hydroxybutanoate (2.0 g, 16.9 mmol) were added. The hydrogen pressure of the reactor was increased to 500 psig, the reactor was stirred for 1 hour at room temperature, and hydrogen gas was then removed. The evacuation and filling with nitrogen were repeated three times. Then, the Parr autoclave was filled with oxygen to a pressure of 60 bar. The reaction mixture was allowed to react for 48 hours while maintaining a temperature of 80° C. The resulting product was analyzed by gas chromatography, GC-MS and $^1$H-NMR (Table 4).

TABLE 4

| Ex. | HBM[b] PtO$_2$ | P$_{O2}$ (bar) | Temp. (° C.) | Time (h) | Conversion (%) | Selectivity (%) | Condition[a] |
|---|---|---|---|---|---|---|---|
| 21B | 100:1 | 60 | 80 | 48 h | 47 | 99 | H$_2$: 500 psig for 1 h |
| 21C | 50:1 | 60 | 80 | 48 h | 81 | 99 | H$_2$: 500 psig for 1 h |
| 21D | 20:1 | 60 | 80 | 48 h | 93 | 99 | H$_2$: 500 psig for 1 h |

Note)
[a] reduction condition with platinum oxide (PtO$_2$)
[b] HBM = methyl 3-hydroxybutanoate

EXAMPLE 22

The synthesis of methyl 3-oxopentanoate

In a 45 ml Parr autoclave purged with nitrogen, platinum oxide hydrate (0.17 g) and methyl 3-hydroxypentanoate (2.0 g, 15.1 mmol) obtained from Example 12 were added. The hydrogen pressure of the reactor was increased to 500 psig, the reactor was stirred for 1 hour at room temperature, and hydrogen gas was then removed. The evacuation and filling with nitrogen were repeated three times. Then, the Parr autoclave was filled with oxygen to the pressure of 60 bar. The reaction mixture was allowed to react for 48 hours while maintaining a temperature of 80° C. The resulting product was analyzed by gas chromatography, GC-MS and $^1$H-NMR; conversion 82%, selectivity 91%.

EXAMPLE 23

The synthesis of methyl 4-chloroacetoacetate

In a 45 ml Parr autoclave purged with nitrogen, platinum oxide hydrate (0.15 g) and methyl 3-hydroxy-4-chlorobutanoate (2.0 g, 13.2 mmol) obtained from Example 13 were added. The hydrogen pressure of the reactor was increased to 500 psig, the reactor was stirred for 1 hour at room temperature, and hydrogen gas was then removed. The evacuation and filling with nitrogen were repeated three times. Then, the Parr autoclave was filled with oxygen to a pressure of 60 bar. The reaction mixture was allowed to react for 48 hours while maintaining a temperature of 80° C. The resulting product was analyzed by gas chromatography, GC-MS and $^1$H-NMR; conversion 77%, selectivity 86%.

EXAMPLE 24

The synthesis of methyl 3-oxo-4-phenylbutanoate

In a 45 ml Parr autoclave purged with nitrogen, platinum oxide hydrate (0.12 g) and methyl 3-hydroxy-4-phenylbutanoate (2.0 g, 10.3 mmol) obtained from Example 15 were added. The hydrogen pressure of the reactor was increased to 500 psig, the reactor was stirred for 1 hour at room temperature, and hydrogen gas was then removed. The evacuation and filling with nitrogen were repeated three times. Then, the Parr autoclave was filled with oxygen to a pressure of 60 bar. The reaction mixture was allowed to react for 48 hours while maintaining a temperature of 80° C. The resulting product was analyzed by gas chromatography, GC-MS and $^1$H-NMR; conversion 65%, selectivity 83%.

The present invention provides a process for preparing malonate derivatives or β-ketoesters in a high yield, which comprises the step of reacting an epoxide derivative with carbon monoxide and an alcohol in the presence of a catalyst system consisting of a cobalt catalyst and a promoter to effectively produce a β-hydroxyester, and oxidizing the resulting β-hydroxyester. Further, the present invention provides a catalyst system having a high activity and selectivity, which allows preparation of malonate derivatives or β-ketoesters in a high yield. In addition, due to the use of imidazole or its derivatives as the promoter, the present invention provides a novel process for preparing malonate derivatives or β-ketoesters with a reduced catalyst cost.

We claim:

1. A process for preparing a malonic acid monoester or β-ketoester from an epoxide, comprising:
    (a) reacting an epoxide with carbon monoxide and an alcohol in the presence of a catalytic amount of a cobalt compound and at least one promoter selected from the group consisting of imidazole derivatives to produce a β-hydroxyester;
    (b) separating the β-hydroxyester from the cobalt compound and the promoter; and
    (c) oxidizing the β-hydroxyester to produce a malonic acid monoester or β-ketoester.

2. The process according to claim 1, wherein the imidazole derivatives are represented by the following formula (I):

(I)

wherein R$_5$, R$_6$, R$_7$ and R$_8$ are independently a hydrogen atom; a C$_{1-10}$ linear or branched alkyl, C$_{5-10}$ cycloalkyl, C$_{6-10}$ alkylcycloalkyl, C$_{6-10}$ (cycloalkyl)alkyl, C$_{7-10}$ alkaryl or C$_{7-10}$ aralkyl group which is unsubstituted or substituted with a hydroxy group; F; Cl; a C$_{1-3}$ a hydroxy group. alkoxy group; or a hydroxy group.

3. The process according to claim 1, wherein the molar ratio of the promoter to the cobalt compound is in the range from about 0.01:1 to about 100:1.

4. The process according to claim 1, wherein the epoxide is represented by the following formula (II):

(II)

wherein R$_1$ and R$_2$ are independently a hydrogen atom; a C$_{1-20}$ linear or branched alkyl group, a C$_{5-10}$ cycloalkyl group, a C$_{6-20}$ alkylcycloalkyl group, a C$_{6-20}$ (cycloalkyl)alkyl group, a C$_{7-20}$ aralkyl group, or a C$_{7-20}$ alkaryl group, each of which can be unsubstituted or substituted with at least one F, Cl or Br; or a C$_{6-20}$ aryl group which is unsubstituted or substituted with at least one F, Cl, amine group, nitrile group or alkoxy group.

5. The process according to claim 1, wherein the alcohol is represented by the formula R$_3$OH, in which R$_3$ is C$_{1-20}$ linear or branched alkyl group, a $C_{5-20}$ cycloalkyl group, a $C_{6-20}$ aryl group, a $C_{7-20}$ alkaryl group or a $C_{7-20}$ aralkyl group.

6. The process according to claim 5, wherein the alcohol is selected from the group consisting of methanol, ethanol, isopropanol, cyclohexyl alcohol and benzyl alcohol.

7. The process according to claim 1, wherein (a) is carried out using a solvent in addition to the alcohol.

8. The process according to claim 7, wherein the additional solvent is selected from the group consisting of ether compounds represented by the following formulas (III)–(V):

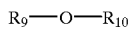
(III)

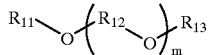
(IV)

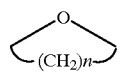
(V)

wherein $R_9$, $R_{10}$, $R_{11}$, $R_{12}$ and $R_{13}$ are independently a $C_{1-10}$ unbranched or branched alkyl group, a $C_{5-10}$ cycloalkyl group, a $C_{6-10}$ alkylcycloalkyl group, a $C_{6-10}$ (cycloalkyl)alkyl group, a $C_{7-10}$ aralkyl group, or a $C_{7-10}$ alkaryl group; m is an integer from 1 to 10; and n is an integer from 2 to 5.

9. The process according to claim 1, wherein (a) is carried out at a temperature from about 30 to about 150° C. under a pressure from about 50 to about 3000 psig.

10. The process according to claim 1, wherein in (a) the β-hydroxyester is produced in an amount of about 2% to about 98%.

11. The process according to claim 1, wherein (c) is carried out at a temperature from about 10 to about 350° C. under a pressure from about 5 to about 3000 psig.

12. The process according to claim 1, wherein in (c) the β-hydroxyester is oxidized in the presence of an oxidizing catalyst.

13. The process according to claim 12, wherein the oxidizing catalyst is selected from the group consisting of platinum, platinum obtained from reduction of platinum oxide with hydrogen, palladium, Raney nickel, said metals supported on solid materials, $H_2PtCl_6$, and $Pt(NH_3)_4(OH)_2$.

14. The process according to claim 12, wherein in (c) the ratio of the oxidizing catalyst to the β-hydroxyester is in the range from about 1:10 to about 1:1000.

15. The process according to claim 1, wherein (c) is carried out in the presence of a promoter.

16. The process according to claim 15, wherein the promoter is selected from the group consisting of Bi, Pb, an oxide, carbonate or phosphate form thereof, and a mixture of 1,10-phenanthroline and a dialkyl diazodicarboxylate.

17. The process according to claim 15, wherein the ratio of the promoter to the oxidizing catalyst to the promoter is in the range from about 0:1 to about 10:1.

18. The process according to claim 15, wherein after (c) the oxidizing catalyst and the promoter are recycled.

19. The process according to claim 1, wherein in (c) the reaction is carried out using an additional solvent selected from the group consisting of water, ethyl acetate, tetrahydrofuran and dioxane.

20. The process according to claim 1, further comprising reacting the malonic acid monoester in the presence of an acid or base with an alcohol of the formula $R_4$—OH, wherein $R_4$ is a $C_{1-10}$ unbranched or branched alkyl group, a $C_{5-10}$ cycloalkyl group, a $C_{6-10}$ alkylcycloalkyl group, a $C_{6-10}$ (cycloalkyl)alkyl group, or a $C_{7-10}$ aralkyl group to yield a malonic acid diester.

21. The process according to claim 1, further comprising hydrolyzing the malonic acid monoester in the presence of an acid to yield malonic acid.

22. The process according to claim 1, further comprising hydrolyzing the malonic acid monoester in the presence of a base to yield a malonic acid dianion.

23. The process according to claim 1, further comprising reacting the malonic acid monoester with an alkaline base to form a salt of the malonic acid monoester.

24. The process according to claim 20, wherein the acid is selected from the group consisting of sulfuric acid, hydrochloric acid, nitric acid, acetic acid, HF, $H_3PO_4$, perchloric acid, p-toluenesulfonic acid, trifluoromethylsulfonic acid, and acidic polymers.

25. The process according to claim 20, wherein the base is selected from the group consisting of pyridine, sodium hydroxide, potassium hydroxide, sodium bicarbonate, sodium carbonate, potassium carbonate, calcium hydroxide, and basic polymers.

26. The process according to claim 20, wherein the reaction in the presence the acid or base is carried out at temperature ranging from about 20 to about 110° C.

* * * * *